United States Patent [19]

Paerels et al.

[11] Patent Number: 4,550,205
[45] Date of Patent: Oct. 29, 1985

[54] DIPHENYL ETHERS HAVING HERBICIDAL ACTIVITY

[75] Inventors: Gerard B. Paerels; Cornelis W. Raven, both of Weesp, Netherlands

[73] Assignee: Duphar International Research B.V., Weesp, Netherlands

[21] Appl. No.: 439,185

[22] Filed: Nov. 4, 1982

[30] Foreign Application Priority Data

Nov. 9, 1981 [NL] Netherlands ............... 8105047

[51] Int. Cl.$^4$ ............... C07C 103/28; C07C 103/34; C07C 69/612; A01N 37/18
[52] U.S. Cl. ............... 564/166; 71/88; 71/94; 71/98; 71/100; 71/111; 71/118; 260/455 R; 260/502.6; 544/126; 544/167; 546/281; 546/296; 546/297; 546/298; 546/302; 548/530; 560/9; 560/21; 562/426; 562/435; 564/150; 564/154; 564/157; 564/162
[58] Field of Search ............... 564/150, 154, 157, 162, 564/166; 71/118; 260/455 R, 502.6; 544/126, 167; 546/281, 296, 297, 298, 302; 548/530; 560/9, 21; 562/426, 435

[56] References Cited

U.S. PATENT DOCUMENTS

| | | | |
|---|---|---|---|
| 3,839,444 | 10/1974 | Thirssen | 564/166 |
| 4,134,753 | 1/1979 | Hörlein et al. | 564/166 X |
| 4,209,318 | 6/1980 | Johnson | 71/118 X |
| 4,364,875 | 12/1982 | Sehring et al. | 560/21 X |
| 4,384,135 | 5/1983 | Cartwright et al. | 564/166 X |
| 4,426,220 | 1/1984 | Parg et al. | 71/118 X |
| 4,515,628 | 5/1985 | Yoshimoto et al. | 560/21 X |

FOREIGN PATENT DOCUMENTS

| | | | |
|---|---|---|---|
| 2938595 | 4/1981 | Fed. Rep. of Germany | 71/118 |
| 1001441 | 1/1976 | Japan | 71/118 |
| 0072946 | 5/1982 | Japan | 560/21 |

OTHER PUBLICATIONS

Paerels et al., CA 99:212909x (1983).

Primary Examiner—Thomas A. Waltz
Attorney, Agent, or Firm—Stevens, Davis, Miller & Mosher

[57] ABSTRACT

The invention relates to new diphenyl ethers of the general formula

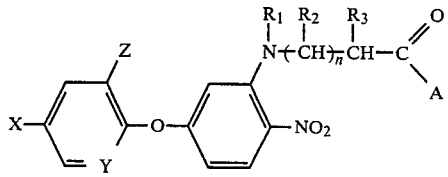

wherein
X is a hydrogen atom, a halogen atom, a nitro group, an optionally halogenated alkyl, alkoxy or alkylthio group having 1–6 carbon atoms, or an alkanoyl group having 1–4 carbon atoms;
Y is a nitrogen atom or a group of the formula CH or CCl;
Z is a hydrogen atom, a halogen atom, a nitro group, an optionally halogenated alkyl group having 1–4 carbon atoms, or an alkanoyl group having 1–4 carbon atoms; n is 0–2;
$R_1$ is a hydrogen atom, or an alkyl or alkanoyl group having 1–4 carbon atoms;
$R_2$ and $R_3$ are equal or different and represent hydrogen atoms or alkyl groups having 1–4 carbon atoms; and
A is a group of the general formula

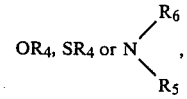

wherein
$R_4$ is a hydrogen atom, an alkyl group having 1–6 carbon atoms, or a cation of an alkali metal, alkaline earth metal or an alkylated or non-alkylated ammonium group, and
$R_5$ and $R_6$ are equal or different and represent hydrogen atoms, dialkylamino groups wherein the alkyl groups each have 1–4 carbon atoms, alkyl groups having 1–4 carbon atoms, or wherein $R_5$ and $R_6$ together with the nitrogen atom to which they are bound can form a heterocyclic ring which may comprise a second hetero atom selected from O, S or N;

with the provisos, that X and Z are not both hydrogen atoms or nitro groups, and that if A is a group of the formula $OR_4$ $R_1$ is not an alkyl group.

The compounds have a herbicidal activity. After having been processed to compositions, the compounds may be used for controlling undesired plants or for leaf-desiccation in agricultural and horticultural crop in a dosage from 0.01 to 5 kg of active substance per hectare.

4 Claims, No Drawings

DIPHENYL ETHERS HAVING HERBICIDAL ACTIVITY

The invention relates to new diphenyl ethers and to a method of preparing the new compounds. The invention also relates to herbicidal compositions and to compositions for leaf-desiccation on the basis of the new compounds. The invention further relates to the use of these compositions for controlling undesired plants and for leaf-desiccation in agricultural and horticultural crop.

It is known that diphenyl ethers with a certain substitution pattern are suitable to control weeds in agricultural and horticultural crops. This control of weeds may take place after of before the emergence of the weeds; agents whose object it is to control the weed after the emergence thereof are termed post-emergence herbicides, the other ones are termed pre-emergence herbicides. For an unhindered growth of the crop during the whole growth period, both types of herbicides are used, if desired, but one single application is preferred, however, which, when a pre-emergence herbicide is used, usually is carried out simultaneously with or immediately after the sowing of the crop and, when a post-emergence herbicide is used, usually is carried out before the emerged weed starts hindering the growth of the crop. The advantage of the use of pre-emergence herbicides is that they can be provided in the soil destined for the crop simultaneously with the sowing of the crop; this is labour-saving, while damage to the standing crops upon application in a later stage is avoided. On the other hand, post-emergence herbicides are often more effectively active and can hence be used in smaller quantities to be able to effectively control the weed.

It stands to reason that the selectivity of the herbicide used is of the utmost importance. As a matter of fact, the undesired plants must be controlled, c.q. the growth of undesired plants must be suppressed, while the growth of the crop may not be detrimentally influenced by the herbicide used. An ideal herbicide must control the weed in the crop during the whole growth season after one single application in a small dosage. The herbicide should be capable not only of controlling all types of weeds, but also killing both the seedlings and full-grown plants of these weeds, as well as preventing the germination of the weed seeds. Nevertheless, the herbicide may not be phytotoxic with respect to the crops on which it is provided. Of course, none of the herbicides now in use is ideal. An effective weed control is usually associated with too large a phytotoxicity with respect to the crop, while a herbicide which has no detrimental influence whatsoever on the crop in a given dosage, does usually not control all weeds effectively in the same dosage.

Diphenyl ethers having herbicidal properties are known from U.S. Patent Specification No. 4,039,588. As examples of these compounds are stated p-nitrodiphenyl ethers which in the ortho position have an amino substituent with respect to the nitro group, for example, 2,4-dichloro-3'-isopropylamino-4'-nitrodiphenyl ether. As will become apparent from the examples, however, the activity of this herbicidal compound leaves to be desired. Another chemically related diphenyl ether, viz. N-methyl-2-[N-(2-nitro-5-phenoxy-6-chloro)anilino]propionamide, known from European Patent Application No. 0027555, shows hardly any herbicidal activity as will appear from the examples.

Other related compounds, viz. 2-chloro-4-trifluoromethyl-3'-ethylamino-4'-nitrodiphenylether and the corresponding 3'-methylamino compound, are known from the Netherlands patent application No. 7301194. These knwon compounds are also less active than chemically related new compounds according to the invention, as will become apparent from the examples. Moreover, the last-mentioned known compounds do not degrade sufficiently fast in the soil, as opposed to compounds of the present invention.

It is the object of the invention to provide herbicides which can selectively control undesired plants in agricultural and horticultural crops and simultaneously have an improved activity as compared with the above-mentioned known compounds. This object can be achieved by means of new diphenyl ethers of the general formula

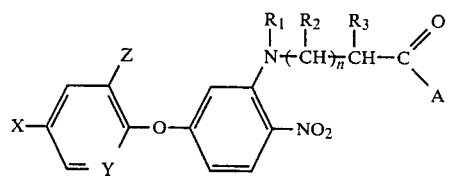

wherein
X is a hydrogen atom, a halogen atom, a nitro group, an optionally halogenated alkyl, alkoxy or alkylthio group having 1–6 carbon atoms, or an alkanoyl group having 1–4 carbon atoms;
Y is a nitrogen atom or a group of the formula CH or CCl;
Z is a hydrogen atom, a halogen atom, a nitro group, an optionally halogenated alkyl group having 1–4 carbon atoms, or an alkanoyl group having 1–4 carbon atoms;
n is 0–2;
$R_1$ is a hydrogen atom, or an alkyl or alkanoyl group having 1–4 carbon atoms;
$R_2$ and $R_3$ are equal or different and represent hydrogen atoms or alkyl groups having 1–4 carbon atoms; and
A is a group of the general formula

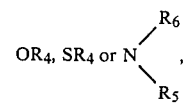

wherein
$R_4$ is a hydrogen atom, an alkyl group having 1–6 carbon atoms, or a cation of an alkali metal, alkaline earth metal or an alkylated or non-alkylated ammonium group, and
$R_5$ and $R_6$ are equal or different and represent hydrogen atoms, dialkylamino groups wherein the alkyl groups each have 1–4 carbon atoms, alkyl groups having 1–4 carbon atoms, or wherein $R_5$ and $R_6$ together with the nitrogen atom to which they are bound can form a heterocyclic ring which may comprise a second hetero atom selected from O, S or N;
with the provisos, that X and Z are not both hydrogen atoms or nitro groups, and that if A is a group of the formula $OR_4$ $R_1$ is not an alkyl group.

Particularly suitable have proved new compounds of the general formula

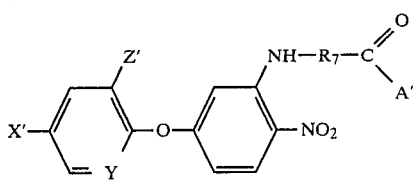

wherein

Y has the above meaning;

X' is a chlorine atom, a nitro group or a trifluoromethyl group;

Z' is a chlorine atom or a nitro group, with the proviso, that not both X' and Z' are nitro groups, $R_7$ is an ethylidene or ethylene group, and A' is a group of the general formula

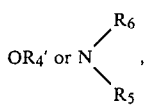

wherein $R_5$ and $R_6$ have the meanings given above, and $R_4'$ is an alkyl group having 1-4 carbon atoms.

Compounds of the general formula

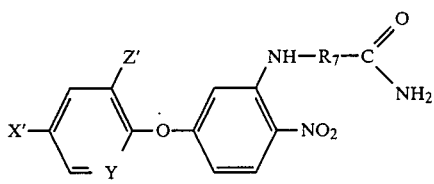

wherein Y,X', Z' and $R_7$ have the above meanings, are to be preferred.

2-[N-{2-nitro-5-(2-chloro-4-trifluoromethylphenoxy)phenyl}amino]propionamide (1) has proved to be excellently suitable for use as an active substance in compositions having a selective herbicidal activity. Other examples of new diphenyl ethers according to the invention which may be used as selective herbicides are:

(2) methyl 2-[N-{2-nitro-5-(2-chloro-4-trifluoromethylphenoxy)phenyl}amino]propionate, (3) ethyl N-[2-nitro-5-(2,4-dichlorophenoxy)phenyl]amino acetate, (4) N-[2-nitro-5-(2,4-dichlorophenoxy)phenyl]aminoacetamide, (5) ethyl N-[2-nitro-5-(2,4,6-trichlorophenoxy)phenyl]amino acetate, (6) 2-[N-{2-nitro-5-(2,4,6-trichlorophenoxy)phenyl}amino]propionic acid, (7) methyl 2-[N-{2-nitro-5-(2,4,6-trichlorophenoxy)phenyl}amino]propionate, (8) ethyl 2-[N-{2-nitro-5-(2,4,6-trichlorophenoxy)phenyl}amino]propionate, (9) 2-[N-{2-nitro-5-(2,4,6-trichlorophenoxy)phenyl}amino]propionamide,

(10) ethyl N-[2-nitro-5-(2-chloro-4-trifluoromethylphenoxy)phenyl]aminoacetate,

(11) 2-[N-{2-nitro-5-(4-methylphenoxy)phenyl}amino]propionamide,

(12) 2-[N-{2-nitro-5-(4-tert.-butylphenoxy)phenyl}amino]propionamide,

(13) methyl 2-[N-{2-nitro-5-(2-methyl-4-chlorophenoxy)phenyl}amino]propionate,

(14) 2-[N-{2-nitro-5-(2-methyl-4-chlorophenoxy)phenyl}amino]propionamide,

(15) ethyl N-[2-nitro-5-(2-chloro-4-trifluoromethylphenoxy)phenyl]-N-acetylaminoacetate,

(16) N-methyl-2-[N-{2-nitro-5-(2-chloro-4-trifluoromethylphenoxy)phenyl}amino]propionamide,

(17) 2-[N-{2-nitro-5-(2-chloro-4-trifluoromethylphenoxy)phenyl}amino]propionic acid,

(18) ethyl 2-[N-{2-nitro-5-(2-chloro-4-trifluoromethylphenoxy)phenyl}amino]propionate,

(19) isopropyl 2-[N-{2-nitro-5-(2-chloro-4-trifluoromethylphenoxy)phenyl}amino]propionate,

(20) n-butyl 2-[N-{2-nitro-5-(2-chloro-4-trifluoromethylphenoxy)phenyl}amino]propionate,

(21) N,N-dimethyl-2-[N-{2-nitro-5-(2-chloro-4-trifluoromethylphenoxy)phenyl}amino]propionamide,

(22) N,N-dimethylamino-2-[N-{2-nitro-5-(2-chloro-4-trifluoromethylphenoxy)phenyl}amino]propionamide,

(23) methyl 3-[N-{2-nitro-5-(2-chloro-4-trifluoromethylphenoxy)phenyl}amino]propionate,

(24) N-[N-{2-nitro-5-(2-chloro-4-trifluoromethylphenoxy)phenyl}alanyl]morpholine,

(25) N-[N-{2-nitro-5-(2-chloro-4-trifluoromethylphenoxy)phenyl}alanyl]pyrrolidine,

(26) 2-[N-{2-nitro-5-(4-bromophenoxy)phenyl}amino]propionamide,

(27) methyl 2-[N-{2-nitro-5-(2,4-dibromophenoxy)phenyl}amino]propionate,

(28) 2-[N-{2-nitro-5-(2,4-dibromophenoxy)phenyl}amino]propionamide,

(29) N-[2-nitro-5-(2,4-dichlorophenoxy)phenyl]-N-ethylaminoacetamide,

(30) methyl 2-[N-{2-nitro-5-(2,4-dichlorophenoxy)phenyl}amino]propionate,

(31) ethyl N-[2-nitro-5-(2-nitro-4-trifluoromethylphenoxy)phenyl]aminoacetate,

(32) methyl 2-[N-{2-nitro-5-(2-nitro-4-trifluoromethylphenoxy)phenyl}amino]propionate,

(33) N-[2-nitro-5-(2-nitro-4-trifluoromethylphenoxy)phenyl]aminoacetamide,

(34) methyl 2-[N-{2-nitro-5-(2-trifluoromethyl-4-nitrophenoxy)phenyl}amino]propionate,

(35) methyl 2-[N-{2-nitro-5-(2-chloro-4-nitrophenoxy)phenyl}amino]propionate,

(36) methyl 2-[N-{2-nitro-5-(2-chloro-4-acetylphenoxy)phenyl}amino]propionate,

(37) methyl 2-[N-{2-nitro-5-(3,5-dichloro-pyridyl-2-oxy)phenyl}amino]propionate,

(38) 2-[N-{2-nitro-5-(2,6-dichloro-4-trifluoromethylphenoxy)phenyl}amino]propionic acid,

(39) methyl 2-[N-{2-nitro-5-(2,6-dichloro-4-trifluoromethylphenoxy)phenyl}amino]propionate,

(40) 2-[N-{2-nitro-5-(2-chlorophenoxy)phenyl}amino]propionamide,

(41) 2-[N-{2-nitro-5-(4-(1,1,2,2-tetrafluoroethoxy)phenoxy)phenyl}amino]propionamide,

(42) 3-[N-{2-nitro-5-(2,4-dichlorophenoxy)phenyl}amino]propionic acid, and

(43) methyl 3-[N-{2-nitro-5-(2,4-dichlorophenoxy)phenyl}amino]propionate.

The substances according to the invention may be used for the control of undesired plants in agricultural and horticultural crops. Although the new diphenyl ethers have an interesting pre-emergence herbicidal activity, their activity as post-emergence herbicides is most striking. Therefore, the compounds according to the invention may be used as post- and as pre-emergence herbicides. The new diphenyl ethers may be used for the control of monocotyle and in particular dicotyle weeds, for example, *Galinsoga parviflora* (small-flowered g.), *Galium aparine* (cleavers), *Chenopodium album* (common lambsquarters), *Polygonum convolvulus* (wild buckwheat), *Capsella bursa-pastoris* (shepard's purse), *Stellaria media* (chickweed), *Senecio vulgaris* (common groundsel), *Veronica arvensis* (corn speedwell), *Matricaria maritima* (chamomile), *Amaranthus retroflexus* (redroot pigweed), *Solanum nigrum* (black nightshade), *Spergula arvensis* (corn spurrey), *Urtica dioica* (stinging nettle), *Polygonum aviculare* (knotgrass), *Silybum marianum* (milk thistle), *Xanthium pensylvanicum*, *Datura stramonium*, *Ipomoea mericata*, *Ipomoea hederacea*, *Ipomoea lucunosa*, *Cassia obtusifolia*, *Sida spinosa*, *Anoda cristata*, *Abutilon theophrasti* and *Portulaca oleracea* in various crops, such as in cereals, for example, wheat, rice, maize, oats and barley, in leguminosae, for example, bean, pea, soya, peanut and lucerne, and in pastureland.

As a special aspect of the invention it has been found that the new substances according to the invention can be used successfully in compositions for leaf-desiccation.

Desiccation or defoliation of a crop prior to harvest may have several advantages. In seed crops it hastens maturity of the seeds by which harvest can be carried out earlier allowing double cropping of the area or preventing harvest under unfavourable conditions e.g. frost, rains, etc. Mechanical harvest is made much more efficient by desiccating or defoliating the crop prior to harvest. Furthermore it can be a great help in preventing infection of the product harvested by diseases present on the vegetative plant parts. Desiccation or defoliating a crop before harvest therefore may nave marked effects on crop yield and quality. In potatoes as much as possible of the above ground plant part is eliminated by desiccation in order to prevent infection of the potato tubers by diseases present on the vegetative plant parts and in order to facilitate mechanical harvesting. Mechanical harvest in cotton requires the complete removal or drying of the leaves for satisfactory results. Desiccation or defoliation furthermore accelerates drying and opening of the green cotton bolls without a deleterious effect on bolls already open.

For practical use, the substances according to the invention are processed to compositions. In such compositions the active substance is mixed with solid carrier material, if desired in combination with auxiliary substances, for example, emulsifiers, wetting agents, dispersing agents and stabilizers.

Examples of compositions according to the invention are aqueous solutions and dispersions, oily solutions and oily dispersions, solutions in organic solvents, pastes, dusting powders, dispersible powders, miscible oils, granules, pellets and aerosol compositions.

Dispersible powders, pastes and miscible oils are compositions in concentrate form which are diluted prior to or during use.

The solutions in organic solvents are mainly used in air application, namely when large areas are treated with a comparatively small quantity of composition. The solutions of the active substance in organic solvents may be provided with a phytotoxicity-reducing substance, for example, wool fat, wool fatty acid or wool fatty alcohol.

A few forms of composition will be described in greater detail hereinafter by way of example.

Granular compositions are prepared by taking up, for example, the active substance in a solvent or dispersing it in a diluent and impregnating the resulting solution/suspension, if desired in the presence of a binder, or granular carrier material, for example porous granules (for example pumice and attaclay), mineral non-porous granules (sand or ground marlow), organic granules (for example, dried coffee grounds, cut tobaccostems or ground corncobs). A granular composition can also be prepared by compressing the active substance together with powdered minerals in the presence of lubricants and binders and disintegrating the compressed product to the desired grain size and sieving it. Granular compositions can be prepared in a different manner by mixing the active substance in powder form with powdered fillers, and glomulating the mixture then to the desired particle size.

Dusting powders can be obtained by intimately mixing the active substance with an inert solid powdered carrier material, for example, talcum.

Dispersible powders are prepared by mixing 10 to 80 parts by weight of a solid inert carrier, for example kaolin, dolomite, gypsum, chalk, bentonite, attapulgite, colloidal $SiO_2$ or mixtures of these and similar substances, with 10 to 80 parts by weight of the active substance, 1 to 5 parts by weight of a dispersing agent, for example the lignine sulphonates or alkylnaphthalene sulphonates known for this purpose, preferably also 0.5 to 5 parts by weight of a wetting agent, for example, fatty alcohol sulphates, alkyl aryl sulphonates, fatty acid condensation products, or polyoxyethylene compounds, and finally, if desired, other additives.

For the preparation of miscible oils the active compound is dissolved in a suitable solvent which preferably is poorly water-miscible, and one or more emulsifiers are added to this solution. Suitable solvents are, for example, xylene, toluene, petroleum distillates which are rich in aromates, for example, solvent naphtha, distilled tar oil and mixtures of these liquids. As emulsifiers may be used, for example, polyoxyethylene compounds and/or alkyl aryl sulphonates. The concentration of the active compound in these miscible oils is not restricted to narrow limits and may vary, for example, between 2 and 50% by weight. In addition to a miscible oil may also be mentioned as a liquid and highly concentrated primary composition a solution of the active substance in a readily water-miscible liquid, for example, a glycol, a glycol ether, dimethylformamide, or N-methylpyrrolidone, to which solution a dispersing agent and, if desired, a surface-active substance has been added. When diluting with water shortly before or during spraying, an aqueous dispersion of the active substance is then obtained.

An aerosol composition according to the invention is obtained in the usual manner by incorporating the active substance, if desired in a solvent, in a volatile liquid to be used as a propellant, for example, a mixture of chlorine-fluorine derivatives of methane and ethane, a mixture of lower hydrocarbons, dimethyl ether, or gases such as carbon dioxide, nitrogen and nitrous oxide.

In addition to the above-mentioned ingredients, the agents according to the invention may also contain other substances known for use in this type of agents, For example, a lubricant, for example, calcium stearate or magnesium stearate, may be added to a dispersible powder or a mixture to be granulated. "Adhesives", for example, polyvinylalcohol, cellulose derivatives or other colloidal materials, such as casein, may also be added so as to improve the adhesion of the pesticide to the crop. Furthermore, a substance may be added to reduce the phytotoxicity of the active substance, carrier material or auxiliary substance, for example, wool fat or wool fatty alcohol.

Growth regulating and pesticidal compounds known per se may also be incorporated in the compositions according to the invention. As a result of this the activity spectrum of the composition is widened and synergism may occur. In addition foliar fertilizers may be present.

For use in such a combination composition are to be considered, in addition to insecticidal and acaricidal compounds known per se, the following known growth regulating and fungicidal compounds:

Growth regulators, for example:
1. higher alcohols, for example, octanol and decanol;
2. lower esters of fatty acids;
3. ethylene-generators, for example, (2-chloroethyl)-phosphonic acid and 2-chloroethyl-tris(2-methoxyethoxy)silane;
4. nitrodiphenylethers;
5. substituted dinitroanilines, for example, 2-chloro-N-ethyl-6-fluoro-N-[2,6-dinitro-4-(trifluoromethyl)-phenyl]benzenemethaneamine;
6. trifluoromethylsulphonylamino compounds;
7. piperidinederivatives;
8. benzylthiocarbamates, for example, benzyl N,N'-dipropylthiocarbamate;
9. phosphorothionoamidates and amidothionophosphonic acid esters;
10. benzoxazoles; and furthermore: maleic hydrazide; 2,3:4,6-di-O-isopropylidene-α-xylo-2-hexulo-furanosonic acid-sodium; N,N-dimethylaminosuccinic acid; α-cyclopropyl-4-methoxy-α-(pyrimidin-5-yl)benzyl alcohol; 2-chloroethyltrimethyl ammonium; N,N-di(-phosphonomethyl)glycine; 9-hydroxyfluorene-9-carbonic acid (or ester); 2-chloro-9-hydroxyfluorene-9-carbonic acid (or ester); N-1-naphthylphthalaminic acid; 2,3-dihydro-5,6-diphenyl-1,4-oxathiine; N-(3,4-dimethyl-3-cyclohexenyl)butylamine; and 3,5-dinitro-2,6-dimethyl-4-tert.-butylacetophenone; or mixtures of these compounds.

Fungicides, for example:
1. organic tin compounds, for example, triphenyl tin hydroxide and triphenyl tin acetate;
2. alkylene bisdithiocarbamates, for example, zinc ethylenebisdithiocarbamate and manganese ethylene bisdithiocarbamate;
3. 1-acyl- or 1-carbamoyl-N-benzimidazole(-2)carbamates and 1,2-bis(3-alkoxycarbonyl-2-thiureido)benzene; and furthermore 2,4-dinitro-6-(2-octylphenyl-crotonate), 1-[bis(dimethylamino)phosphoryl]-3-phenyl-5-amino-1,2,4-triazole, N-trichloromethylthiophthalimide, N-trichloromethylthiotetrahydrophthalimide, N-(1,1,2,2-tetrachloroethylthio)-tetrahydrophthalimide, N-dichlorofluoromethylthio-N-phenyl-N,N'-dimethylsulphamide, tetrachloroisophthalonitrile, 2-(4'-thiazolyl)-benzimidazole, 5-butyl-2-ethylamino-6-methylpyrimidine-4-yl-dimethylsulphamate, 1-(4-chlorophenoxy)-3,3-dimethyl-1(1,2,4-triazole-1-yl)-2-butanone, α-(2-chlorophenyl)-α-(4-chlorophenyl)-5-pyrimidinemethanol, 1-(isopropyl-carbamoyl)-3-(3,5-dichlorophenyl)hydantoin, N-(1,1,2,2-tetrachloroethylthio)-4-cyclohexene-1,2-carboximide, N-trichloromethylmercapto-4-cyclohexene-1,2-dicarboximide, N-tridecyl-2,6-dimethylmorpholine, metal salts of ethylphosphite, and N-(2,6-dimethylphenyl-N-methoxyacetyl)alanine methylester, or mixtures of these compounds.

The dosage of the composition according to the invention desired for practical application will, of course, depend on various factos, for example, field of application, active substance chosen, form of composition, nature and size of the weeds and the crops, and the weather conditions.

In general it holds that for herbicidal application favourable results are reached with a dosage which corresponds with 0.01 to 5 kg of active substance per hectare, preferably 0.1 to 3 kg per hectare. For leaf-desiccation a dosage corresponding with 0.1 to 5 kg of active substance per hectare gives good results, preferably 1 to 5 kg per hectare.

It has been found that the herbicidal activity, as well as the effectivity for leaf-desiccation, of the compositions according to the invention may increase considerably by using suitable adjuvants, for example, mineral oils and/or polyoxyethylene compounds, such as the mineral oils and surface-active substances stated in Netherlands Patent Application No. 7613453. Dependent on the application, the quantity of the adjuvant to be used may vary within wide limits and usually is between 10 and 10,000 ml per hectare.

The compounds according to the invention are new substances which can be prepared in a manner known per se for the synthesis of related compounds.

For example, the compounds can be prepared by reacting a compound of the general formula

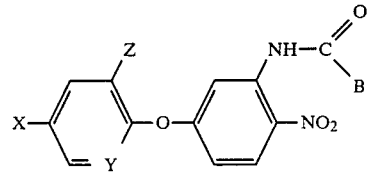

wherein
X,Y and Z have the meanings given before, and
B is a hydrogen atom, or a lower alkyl or alkoxy group,
with a compound of the general formula

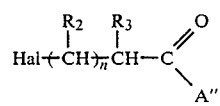

wherein
$R_2$ and $R_3$ have the meanings given before,
Hal is a halogen atom, and
A" is an alkoxy or alkylthiogroup having 1–6 carbon atoms,
followed by a deacylation, after which the resulting product, if desired,
(a) is converted directly or via the corresponding acid chloride, with an amine of the general formula

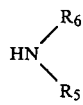

wherein $R_5$ and $R_6$ have the meanings given before, a product being obtained of the first above general formula, wherein A is a group of the general formula

or (b) is hydrolysed with an inorganic acid or base, a product being obtained of the first above general formula, wherein A is a hydroxy or mercapto group, or (c) , after hydrolysis, is converted with an inorganic base, ammonia or a aliphatic amine, a salt being obtained of the first above general formula, wherein A is a group of the general formula $OR_4''$ or $SR_4''$, wherein $R_4''$ is a cation of an alkali metal, alkaline earth metal, or an alkylated or non-alkylated ammonium group.

The reaction with an ester or thio ester of an α- or β-halogen alkane carboxylic acid is usually carried out in two steps. In the first reaction step the amino hydrogen atom is substituted by an alkoxy or alkylthiocarbonylalkyl group while splitting off hydrogenhalide, while in the second reaction step the acyl group or ester group at the nitrogen atom is replaced by a hydrogen atom. Both reaction steps preferably take place in a polar organic solvent, the former, for example, in a dipolar aprotic solvent, such as dimethyl formamide, the latter, for example, in a protic solvent such as acetic acid. The first reaction step is preferably carried out under the influence of an acid binding substance, for example, an inorganic base such as potassium carbonate, the second step, for example, under the influence of a little acid, for example, hydrobromic acid. The hydrolysis reaction of the ester or thio ester thus obtained with an inorganic base or acid is preferably carried out in water, a polar organic solvent or a mixture hereof at a reaction temperature of 0°–50° C; the reaction of the resulting carboxylic acid with inorganic base, ammonia or amine is preferably carried out under the same reaction conditions. The reaction of the resulting ester or thioester with an amine, for example with ammonia, is preferably carried out in an inert polar organic solvent, for example, an alcohol such as methanol or ethanol, at room temperature or a slightly elevated or reduced temperature.

The new compounds of the invention can also be prepared by reacting a compound of the general formula

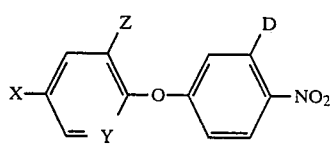

wherein
X, Y and Z have the meanings given before, and

D is a nitro group, a halogen atom, or a substituted or non-substituted aryloxy group,
with an amine of the general formula

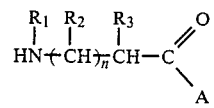

wherein
n, $R_1$, $R_2$, $R_3$ and A have the meanings given before, after which the resulting product of the first above general formula, if A is a hydroxy group or an alkoxy or alkylthio group having 1–6 carbon atoms, if desired, is converted in a manner as described above, into a product of the first above general formula, wherein
(a) A is a group of the general formula

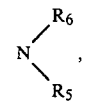

wherein $R_5$ and $R_6$ have the meanings given before,
(b) A is a hydroxy or mercapto group, or
(c) A is a group of the general formula $OR_4''$ or $SR_4''$, wherein $R_4''$ has the meaning given before.

The above reaction is preferably carried out in an inert organic solvent, for example an ether, e.g. dioxane, or a polar solvent, e.g. acetonitril, at a temperature between room temperature and the boiling point of the solvent. A slight amount of a suitable base, e.g. an alkali-metal hydroxide or carbonate, may advance the reaction.

As is obvious from the above the new acid amides of the general formula

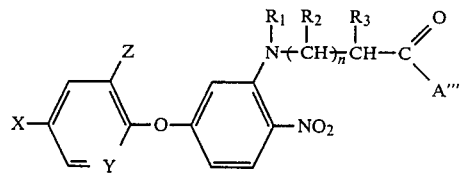

wherein A''' is a group of the general formula

and the other symbols as well as $R_5$ and $R_6$ have the above meanings, can be prepared by reacting a compound of the general formula

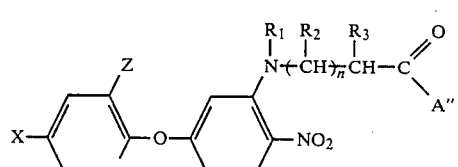

wherein the symbols have the meaning given before, directly or via the corresponding acid chloride with an amine of the general formula

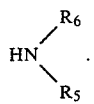

The direct reaction with the amine is preferably carried out in a polar organic solvent or a mixture thereof, at a reaction temperature between 0° C. and the boiling point of the solvent used. If the corresponding acid chloride is prepared intermediately this acid chloride is formed from the corresponding acid by a suitable chlorinating agent such as thionyl chloride. The conversion of the acid chloride into the acid amide is preferably carried out in a polar organic solvent, generally at a reduced temperature.

The invention will now be described in greater detail with reference to the following specific examples.

EXAMPLE I (a) Preparation of methyl 2-[N-acetyl-N-{2-nitro-5-(2-chloro-4-trifluoromethylphenoxy)phenyl}amino]propionate.

22.1 g of potassium carbonate and 10.7 ml (16.0 g) of methyl α-bromopropionate were added successively to a solution of 30 g of 2-nitro-5-(2-chloro-4-trifluoromethylphenoxy)acetanilide in 100 ml of dimethylformamide, after which the mixture was stirred overnight at room temperature. After α-bromopropionic acid ester (4.0 ml) had been added once again, had been stirred at 40° C. for 6 hours, again the same quantity of α-bromopropionic acid ester and 8 g of potassium carbonate had been added and the mixture had been stirred overnight at 40° C., water was added to the reaction mixture, after which the organic material was extracted with methylene chloride. After washing with water, drying, filtering, distilling off the solvent and chromatographing over silica as a filler (chloroform as an eluent), 27.4 g of the desired product were obtained as a yellow syrupy liquid; identification by means of NMR.

In a corresponding manner the following compounds were prepared:

ethyl 2-[N-acetyl-N-{2-nitro-5-(2-chloro-4-trifluoromethylphenoxy)phenyl}amino]propionate; melting-point 87° C.;
ethyl N-acetyl-N-[2-nitro-5-(2,4,6-trichlorophenoxy)-phenyl]amino acetate; melting-point 142° C.;
ethyl 2-[N-acetyl-N-{2-nitro-5-(2,4,6-trichlorophenoxy)phenyl}amino]propionate; melting-point 172° C.;
methyl 2-[N-acetyl-N-{2-nitro-5-(2,4,6-trichlorophenoxy)phenyl}amino]propionate; melting-point 150° C.;
methyl 3-[N-acetyl-N-{2-nitro-5-(2,4-dichlorophenoxy)phenyl amino]propionate;
ethyl N-acetyl-N-[2-nitro-5-(2,4-dichlorophenoxy)-phenyl]amino acetate;
ethyl N-acetyl-N-[2-nitro-5-(2-chloro-4-trifluoromethylphenoxy)phenyl]aminoacetate; melting-point 87° C.;
ethyl 2-[N-acetyl-N-{2-nitro-5-(4-methylphenoxy)-phenyl}amino]propionate;
ethyl 2-[N-acetyl-N-{2-nitro-5-(4-tert.butylphenoxy)-phenyl}amino]propionate;
methyl 2-[N-acetyl-N-{2-nitro-5-(2-methyl-4-chlorophenoxy)phenyl}amino]propionate;
methyl 3-[N-acetyl-N-{2-nitro-5-(2-chloro-4-trifluoromethylphenoxy)phenyl}amino]propionate;
ethyl 2-[N-acetyl-N-{2-nitro-5-(4-bromophenoxy)-phenyl}amino]propionate;
methyl 2-[N-acetyl-N-{2-nitro-5-(2,4-dibromophenoxy)phenyl}amino]propionate;
methyl 2-[N-acetyl-N-{2-nitro-5-(2,4-dichlorophenoxy)phenyl}amino]propionate;
ethyl N-acetyl-N-[2-nitro-5-(2-nitro-4-trifluoromethylphenoxy)-phenyl]aminoacetate;
methyl 2-[N-acetyl-N-{2-nitro-5-(2-nitro-4-trifluoromethylphenoxy)phenyl}amino]propionate;
methyl 2-[N-acetyl-N-{2-nitro-5-(2-trifluoromethyl-4-nitrophenoxy)phenyl}amino]propionate;
methyl 2-[N-acetyl-N-{2-nitro-5-(2-chloro-4-nitrophenoxy)phenyl}amino]propionate;
methyl 2-[N-acetyl-N-{2-nitro-5-(2-chloro-4-acetylphenoxy)phenyl}amino]propionate;
ethyl 2-[N-acetyl-N-{2-nitro-5-(2-chlorophenoxy)-phenyl}amino]propionate; and
ethyl 2-[N-acetyl-N-{2-nitro-5-(4-(1,1,2,2-tetrafluoroethoxy)phenoxy)phenyl}amino]propionate.

(b) Preparation of methyl 2-[N-{2-nitro-5-(2-chloro-4-trifluoromethylphenoxy)phenyl}amino]propionate.

90 Ml of a 45 wt.% solution of hydrobromic acid in acetic acid were added to a solution of 26.1 g of the methyl 2-[N-acetyl-N-{2-nitro-5-(2-chloro-5-trifluoromethylphenoxy)phenyl}amino]propionate, obtained according to Example I (a), in 250 ml of acetic acid. After stirring at 40° C. for 30 hours, water was added to the reaction mixture, after which the organic material was extracted with methylene chloride. After washing with water, drying, filtering, and distilling off the solvent, the residue was dissolved in a mixture of 25 ml of methanol and 10 ml of concentrated sulphuric acid. After refluxing for 1 hour the reaction mixture was substantially evaporated to dryness under reduced pressure, after which ice and water were added. After extraction with dichloromethane, the organic phase was washed with water, dried, filtered and evaporated to dryness under reduced pressure. The resulting syrupy liquid was purified by means of column chromatography with silica as a filler and chloroform as an eluent. The desired product was obtained as a yellow syrup and was identified by means of NMR. The melting point after recrystallization from methanol was 101° C. An elementary analysis yielded the following results: 49.09% C (calculated 48.76), 3.45% H (calculated 3.39), and 6.65% N (calculated 6.69).

In a corresponding manner the following compounds were prepared from the N-acetyl compounds obtained according to Example I (a):
ethyl N-[2-nitro-5-(2-chloro-4-trifluoromethylphenoxy)phenyl]amino acetate; melting point 91° C.;
ethyl N-[2-nitro-5-(2,4,6-trichlorophenoxy)phenyl]amino acetate; melting-point 151°–152° C.;
elementary analysis:
45.68% C (calculated 45.79), 3.06% H (calculated 3.12),
25.46% Cl (calculated 25.34) and 6.62% N (calculated 6.68).
ethyl 2-[N-{2-nitro-5-(2,4,6-trichlorophenoxy)phenyl-}amino]propionate (oil); in addition to free acid;
methyl 2-[N-{2-nitro-5-(2,4,6-trichlorophenoxy)phenyl-}amino]propionate (melting-point 80° C.); in addition to free 2-[N-{2-nitro-5-(2,4,6-trichlorophenoxy)-phenyl}amino]propionic acid (melting-point 234° C.);

ethyl N-[2-nitro-5-(2,4-dichlorophenoxy)phenyl]aminoacetate; melting-point 113° C.; elementary analysis: found 49.86% C (calculated 49.88), found 3.64% H (calculated 3.66), found 18.38% Cl (calculated 18.41), found 7.32% N (calculated 7.27).

methyl 2-[N-{2-nitro-5-(2-methyl-4-chlorophenoxy)-phenyl}amino]propionate; melting-point 121° C.;

methyl 3-[N-{2-nitro-5-(2-chloro-4-trifluoromethyl-phenoxy)phenyl}amino]propionate; melting-point 91° C.;

methyl 2-[N-{2-nitro-5-(2,4,-dibromophenoxy)phenyl}amino]propionate; melting-point 121° C.;

methyl 2-[N-{2-nitro-5-(2,4-dichlorophenoxy)phenyl}amino]propionate; melting-point 122° C.;

ethyl N-[2-nitro-5-(2-nitro-4-trifluoromethylphenoxy)-phenyl]aminoacetate; melting-point 97° C.;

methyl 2-[N-{2-nitro-5-(2-nitro-4-trifluoromethylphenoxy)phenyl}amino]propionate; melting-point 96° C.;

methyl 2-[N-{2-nitro-5-(2-trifluoromethyl-4-nitrophenoxy)phenyl}amino]propionate; syrup;

methyl 2-[N-{2-nitro-5-(2-chloro-4-nitrophenoxy)-phenyl}amino]propionate; syrup; CMR-analysis for $C_6H_3(Cl-2)(NO_2-4)$. $OC_6H_3(NO_2-4).NH(-3)-C^1H(C^2H_3)-C^3O_2C^4H_3$: chemical shift (ppm) $C^1$ 51.4, $C^2$ 18.4; $C^3$ 172.6, $C^4$ 52.8;

methyl 2-[N-{2-nitro-5-(2-chloro-4-acetylphenoxy)-phenyl}amino]propionate; syrup; IR spectrum: $\nu(cm^{-1})=3350$, 1740, 1690, 1630, 1340, 1260, 1220, 750; and methyl 3-[N-{2-nitro-5-(2,4-dichlorophenoxy)phenyl}amino]propionate; syrup; IR spectrum: $\nu(cm^{-1})=3390$, 1732, 1620, 1340, 1265, 1215, 756; in addition to free 3-[N-{2-nitro-5-(2,4-dichlorophenoxy)phenyl}amino]propionic acid; melting point 115° C.

EXAMPLE II

Preparation of 2-[N-{2-nitro-5-(2-chloro-4-trifluoromethylphenoxy)-phenyl}amino]propionamide.

Ammonia was led at room temperature for 28 hours into a solution of 11.7 g of the methyl 2-[N-{2-nitro-5-(2-chloro-4-trifluoromethylphenoxy)phenyl}amino]propionate, obtained according to Example I, in 100 ml of methanol. After evaporating to dryness under reduced pressure and recrystallizing from acetonitrile, an orange crystalline substance was obtained having a melting-point of 187° C. Elementary analysis: 47.67% C (calculated 47.60), 3.24% H (calculated 3.25) and 10.24% N (calculated 10.41).

In a corresponding manner were prepared:

2-[N-{2-nitro-5-(2,4,6-trichlorophenoxy)phenyl}amino]propionamide; melting-point 228°–229° C.; elementary analysis: found 44.58% C (calculated 44.52), found 3.05% H (calculated 2.99), found 26.08% Cl (calculated 26.28), found 10.45% N (calculated 10.38);

N-[2-nitro-5-(2,4-dichlorophenoxy)phenyl]aminoacetamide; melting-point 188° C.;

2-[N-{2-nitro-5-(4-methylphenoxy)phenyl}amino]propionamide; melting-point 160° C.;

2-[N-{2-nitro-5-(4-tert.-butylphenoxy)phenyl}amino]propionamide; melting-point 174° C.;

2-[N-{2-nitro-5-(2-methyl-4-chlorophenoxy)phenyl}amino]propionamide; melting-point 216° C.;

N-methyl-2-[N-{2-nitro-5-(2-chloro-4-trifluoromethylphenoxy)phenyl}amino]propionamide; melting-point 172° C.;

2-[N-{2-nitro-5-(4-bromophenoxy)phenyl}amino]propionamide; melting-point 207° C.;

2-[N-{2-nitro-5-(2,4-dibromophenoxy)phenyl}amino]propionamide; melting-point 236° C.;

N-[2-nitro-5-(2-nitro-4-trifluoromethylphenoxy)phenyl]aminoacetamide; melting-point 201° C.;

2-[N-{2-nitro-5-(4-(1,1,2,2-tetrafluoroethoxy)phenoxy)-phenyl}-amino]propionamide; melting-point 136° C.; and 2-[N-{2-nitro-5-(2-chlorophenoxy)phenyl}amino]propionamide; melting-point 147° C.

EXAMPLE III

Preparation of N-[N-{2-nitro-5-(2-chloro-4-trifluoromethylphenoxy)-phenyl}alanyl]morpholine.

A solution of 8.11 g of 2-[N-{2-nitro-5-(2-chloro-4-trifluoromethylphenoxy)phenyl}amino]propionic acid, prepared by saponification of the corresponding methyl ester, in 16 ml of thionylchloride was heated at 50° C. for 1 hour. After evaporating to dryness under reduced pressure the residue was dissolved in 40 ml of acetonitrile. Under external cooling with ice (temperature below 10° C.) 3,50 g of morpholine was added dropwise. After stirring for 0.5 hour the reaction mixture was concentrated and subsequently water was added. The product was isolated by extraction with methylene chloride, washing and reducing the organic phase. The syrup obtained was recrystallized from a mixture of benzene and cyclohexan (1/1 v/v), yielding 7.50 g of a crystalline material with the desired structure (spectr.); melting-point 190° C.

In a corresponding manner the following compounds were prepared:

N,N-dimethylamino-2-[N-{2-nitro-5-(2-chloro-4-trifluoromethyl-phenoxy)phenyl}amino]propionamide; melting-point 201° C.; and N-[N-{2-nitro-5-(2-chloro-4-trifluoromethylphenoxy)-phenyl}alanyl]pyrrolidine; melting-point 158° C.

EXAMPLE IV

Preparation of 3-[N-{2-nitro-5-(2,4-dichlorophenoxy)phenyl}amino]-propionic acid.

Amounts of 8.90 g of 2,4-bis(2,4-dichlorophenoxy)nitrobenzene, 5.35 g of β-alanine and 11.06 g of $K_2CO_3$ were added to 50 ml acetonitrile. The reaction mixture was refluxed for 5 days. After evaporating the solvent the residue was stirred with 150 ml of water and 100 ml of diethylether for 1 hour. The water phase was acidified with conc. hydrochloric acid and extracted with methylene chloride. After drying and evaporating the solvent the organic layer yielded the desired product as a yellow crystalline material; melting-point 115° C.; yield 2.64 g.

In a corresponding manner, but now using dioxane as the solvent and KOH as the base, N-[2-nitro-5-(2,4-dichlorophenoxy)phenyl]-N-ethylaminoacetamide was prepared; melting-point 140° C.

EXAMPLE V (a) Preparation of 2-[N-{2-nitro-5-(2-chloro-4-trifluoromethylphenoxy)phenyl}amino]propionic acid.

Amounts of 145 g of 1-2-chloro-4-trifluoromethyl phenoxy-3,4-dinitrobenzene, 107 g of α-alanine and 221,2 g of $K_2CO_3$ were added to 500 ml of acetonitril. The reaction mixture was refluxed for 24 hours while stirring. After evaporation of the solvent the residue was dissolved in 2 l of water. After acidification with conc. hydrochloric acid the organic material was extracted with dichloromethane, from which, after drying and evaporation of the solvent, the desired product was obtained in a yield of 150.2 g; yellow crystalline material; melting-point 167° C. (after recrystallization from toluene).

(b) The above acid was esterified as follows: 150.2 g of the compound, prepared according to example V (a), was dissolved in a mixture of 750 ml of methanol and 10 ml of concentrated sulphuric acid. After reflux for 2,5 hours the solvent was evaporated for the greater part, and the residue was dissolved in methylene chloride. The organic phase was washed three times with water, dried and reduced. Recrystallization from methanol yielded methyl 2-[N-{2-nitro-5-(2-chloro-4-trifluoromethylphenoxy)phenyl}amino]propionate in a yield of 121.4 g; melting-point 101° C.; yellow crystalline material.

In a corresponding manner the following compounds were prepared:

N-methyl-2-[N-{2-nitro-5-(2-chloro-4-trifluoromethylphenoxy)phenyl}amino]propionamide; melting-point 172° C.;

2-[N-{2-nitro-5-(2-chloro-4-trifluoromethylphenoxy)phenyl}amino]propionic acid; melting-point 173° C.;

ethyl 2-[N-{2-nitro-5-(2-chloro-4-trifluoromethylphenoxy)phenyl}amino]propionate; syrup;

isopropyl 2-[N-{2-nitro-5-(2-chloro-4-trifluoromethylphenoxy)phenyl}amino]propionate; syrup;

n-butyl 2-[N-{2-nitro-5-(2-chloro-4-trifluoromethylphenoxy)phenyl}amino]propionate; melting-point 45° C.;

N,N-dimethyl-2-[N-{2-nitro-5-(2-chloro-4-trifluoromethylphenoxy)phenyl}amino]propionamide; melting-point 169° C.;

methyl 2-[N-{2-nitro-5-(3,5-dichloro-pyridyl-2-oxy)phenyl}amino]propionate; syrup;

2-[N-{2-nitro-5-(2,6-dichloro-4-trifluoromethylphenoxy)phenyl}amino]propionic acid; melting-point 193° C.; and methyl 2-[N-{2-nitro-5-(2,6-dichloro-4-trifluoromethylphenoxy)phenyl}amino]propionate; melting-point 84° C.

EXAMPLE VI (a) Preparation of a solution of an active substance, namely 2-[N-{2-nitro-5-(2-chloro-4-trifluoromethylphenoxy)phenyl}amino]propionamide, in a water-miscible liquid ("liquid").

10 g of the above active substance were dissolved in a mixture of 10 ml of isoforon and approximately 70 ml of dimethylformamide, after which polyoxyethylene glycol ricinyl ether was added as an emulsifier in a quantity of 10 g.

In a corresponding manner the other active substances were processed to 10 or 20% "liquids".

In a corresponding manner "liquids" were obtained in N-methyl pyrrolidone, dimethylformamide, and a mixture of N-methyl pyrrolidone and isoforon as solvents.

(b) Preparation of a solution of the active substance in an organic solvent

200 Mg of the active substance to be tested were dissolved in 1,000 ml of acetone in the presence of 1.6 g of nonylphenylpolyoxyethylene. This solution was used as a spray liquid.

(c) Preparation of an emulsifiable concentrate of the active substance.

10 g of the active substance to be tested were dissolved in a mixture of 15 ml of isoforon and 70 ml of xylene; to this solution were added 5 g of a mixture of a polyoxyethylene sorbitan ester and an alkyl benzene sulphonate as an emulsifier.

(d) Preparation of a dispersible powder (W.P.) of the active substance.

25 g of the active substance to be tested were mixed with 68 g of kaolin in the presence of 2 g of sodium butylnaphthalene sulphonate and 5 g of lignine sulphonate.

(e) Preparation of a suspension concentrate (flowable) of the active substance.

A mixture of 10 g of the active substance, 2 g of lignine sulphonate and 0.8 g of a sodium alkylsulphate were completed with water until an overall quantity of 100 ml.

(f) Preparation of a granule of the active substance.

7.5 g of active substance, 5 g of sulphite lye and 87.5 g of ground dolomite were mixed, after which the resulting mixture was processed to a granular composition by means of the so-called compacting method.

EXAMPLE VII

Selective control of weeds ("post-emergence") in agricultural and horticultural crops; open-air experiment (field screening).

In a formulation according to example VI (a), compounds according to the invention were used in a quantity of 0.1 kg per hectare on a test plot with the following weeds: *Galinsoga parviflora* (small-flowered g., Gp), *Galium aparine* (cleavers, Ga), *Chenopodium album* (common lambsquarters, Ca), and *Polygonum convolvulus* (wild buckwheat, Pc). The following crops were present in the trial plot: *Triticum aestivum* (wheat, Ta) and *Pisum sativum* (pea, Ps).

The weeds and crops were sown simultaneously. After emergence they were sprayed with a "liquid" poured out in water and obtained according to example VI (a), by means of a Teejet nozzle mounted on a spraying boom of a tractor. The spray liquid was sprayed in a quantity of 500 liters per hectare.

After 14 days the herbicidal activity was evaluated. The results are recorded in Table A. The meanings of the symbols recorded in the Table are as follows:

— = no or hardly any observable damage
± = obvious damage
+ = serious damage
+ + = the plants are dead

TABLE A

Results of open-eair experiment in post-emergence application (field screening); 0.1 kg of active substance per hectare. 2,4-dichloro-3'-isopropylamino-4'-nitrodiphenyl ether = (a)

| compound no. | Activity on | | | | | |
|---|---|---|---|---|---|---|
| | Ta | Ps | Gp | Ga | Ca | Pc |
| (2) | ± | ± | ++ | ++ | ++ | ++ |
| (a) known | ± | ± | ± | + | ++ | ++ |

EXAMPLE VIII

Selective control of weeds ("pre-emergence") in agricultural and horticultural crops; open-air experiment (field-screening).

Compounds according to the invention were used in a formulation obtained according to Example VI (a) in a quantity of 3 kg per hectare against the weeds stated in Example VII; in the trial plot the following crops were sown: *Triticum aestivum* (wheat, Ta), *Pisum sativum* (pea, Ps), and *Glycine max* (soya, Gm). The weeds and croops were sown simultaneously. Before emergence they were sprayed with a "liquid" poured out in water and obtained according to Example VI (a) by means of the spraying apparatus described in Example VII. The spray liquid was sprayed in a quantity of 500 liters per hectare. After 21 days the herbicidal activity was evaluated. The results are recorded in Table B; the meanings of the symbols are the same as in Example VII.

TABLE B

Results open-air experiment in pre-emergence application; 3 kg of active substance per hectare.

| Compound no. | Activity on | | | | | | |
|---|---|---|---|---|---|---|---|
| | Ta | Ps | Gm | Gp | Ga | Ca | Pc |
| (1) | ± | ± | ± | ++ | ++ | ++ | ++ |
| (2) | ± | | | ++ | ++ | ++ | ++ |
| (4) | − | − | − | + | + | ++ | + |
| (8) | − | − | − | + | ++ | + | ± |
| (9) | − | − | − | + | ++ | ++ | ± |

EXAMPLE IX

Selective control of weeds ("post-emergence") in agricultural and horticultural crops; glasshouse experiment.

Compounds according to the invention were used in a formulation obtained according to Example VI (b) in a quantity of 100 g per hectare against the following weeds: *Galinsoga parviflora* (small flowered g. Gp), *Galium aparine* (cleavers, Ga), *Chenopodium album* (common lambsquarters, Ca), and *Polygonum convolvulus* (wild buckwheat, Pc); the following crops were present: *Tritium aestivum* (wheat, Ta), and *Oryza sativa* (rice, Os). The weeds and crops were sown simultaneously. After emergence they were sprayed with a spray liquid obtained according to Example VI (b) by means of a Sata sprayer. After 2 weeks the herbicidal activity was evaluated. The results are recorded in Table C; the meanings of the symbols are the same as in Example VII.

TABLE C

Results glasshouse experiments in post-emergence application; 100 g of active substance per hectare. 2,4-dichloro-3'-isopropylamino-4'-nitrodiphenyl ether=(a)

| Compound no. | Activity on | | | | | |
|---|---|---|---|---|---|---|
| | Ta | Os | Gp | Ga | Ca | Pc |
| (2) | ± | + | ++ | ++ | ++ | ++ |
| (3) | | | ++ | ++ | ++ | ++ |
| (4) | ± | ± | ++ | + | ++ | ++ |
| (5) | ± | ± | ++ | + | ++ | ++ |
| (6) | ± | − | ++ | ++ | ++ | ++ |
| (7) | ± | + | ++ | ++ | ++ | ++ |
| (8) | ± | + | ++ | ++ | ++ | ++ |
| (9) | ± | + | ++ | ++ | ++ | ++ |
| (10) | ± | + | ++ | ++ | ++ | ++ |
| (a) known | ± | + | + | ± | ++ | ++ |

EXAMPLE X

Exactly as described in Example IX compounds according to the invention were tested for the control of weeds ("post-emergence") in the glasshouse.

The results are recorded in Table D; the meanings of the symbols are the same as in Example VII.

TABLE D

Results glasshouse experiments in post-emergence application; 100 g of active substance per hectare.

N-methyl-2-[N-(2-nitro-5-phenoxy-6-chloro)anilino]-propionamide=(b)

| compound no. | Activity on | | | |
|---|---|---|---|---|
| | Ca | Ga | Gp | Pc |
| (1) | ++ | ++ | ++ | ++ |
| (2) | ++ | ++ | ++ | ++ |
| (11) | ++ | ++ | ++ | ++ |
| (12) | ++ | + | ++ | ++ |
| (13) | ++ | ++ | ++ | ++ |
| (14) | ++ | + | ++ | ++ |
| (15) | ++ | ++ | ++ | ++ |
| (16) | ++ | ++ | ++ | ++ |
| (17) | ++ | ++ | ++ | ++ |
| (18) | ++ | ++ | ++ | ++ |
| (19) | ++ | ++ | ++ | ++ |
| (20) | ++ | ++ | ++ | ++ |
| (21) | ++ | ++ | ++ | ++ |
| (22) | ++ | ++ | ++ | ++ |
| (23) | ++ | ++ | ++ | ++ |
| (24) | ++ | ++ | ++ | ++ |
| (25) | ++ | ++ | ++ | ++ |
| (26) | ++ | ++ | ++ | ++ |
| (27) | ++ | + | ++ | ++ |
| (28) | ++ | ++ | ++ | ++ |
| (29) | ++ | + | ++ | ++ |
| (30) | ++ | ++ | ++ | ++ |
| (31) | ++ | ++ | ++ | ++ |
| (32) | ++ | + | ++ | ++ |
| (33) | ++ | ++ | ++ | ++ |
| (35) | ++ | ++ | ++ | ++ |
| (36) | ++ | + | ++ | ++ |
| (37) | ++ | ++ | ++ | ++ |
| (38) | ++ | + | ++ | ++ |
| (39) | ++ | ++ | ++ | ++ |
| (40) | ++ | ++ | ++ | ++ |
| (41) | ++ | + | ++ | ++ |
| (42) | ++ | ++ | ++ | ++ |
| (43) | ++ | ++ | ++ | ++ |
| (b) known | ± | − | − | − |

EXAMPLE XI

Investigation into the stability in the soil of compounds according to the invention in comparison to some known compounds.

A solution of the compound to be examined was added to sandy loam in a concentration of 5 mg of active substance per kg of soil.

After 1 week and 5 weeks respectively samples of the solid were analyzed by extracting the soil with 90% ethanol and then determining the amount of starting substance in the extract with the aid of a suitable analytical method, viz. high-pressure liquid chromatography.

The results are recorded in Table E.

TABLE E 2-chloro-4-trifluoromethyl-3'-ethylamino-4'-nitrodiphenyl ether=(c)

2-chloro-4-trifluoromethyl-3'-methylamino-4'-nitrodiphenyl ether=(d)

| compound no. | % degradation after 1 week | 5 weeks |
|---|---|---|
| (1) | 17 | 48 |
| (2) | 77 | 97 |
| (c) known | 8 | 9 |
| (d) known | 5 | 10 |

Conclusion: The known compounds are too persistent in the soil for agricultural application in a justified manner. The above new compounds according to the invention, on the contrary, degrade sufficiently fast in the soil, so that no detrimental effects on the environment and/or the succeeding crops are to be expected.

EXAMPLE XII

Compounds according to the invention were tested against various weeds in the glasshouse as described in Example IX. For comparison two known compounds were tested, viz. compounds (c) and (d) identified in Example XI.

The compounds were compared in post- and pre-emergence application, so after and before emergence of the weed plants. The results are recorded in Tables F and G respectively. In these tables the weed names are abbreviated as follows:

*Galinsoga parviflora* (small flowered galinsoga): Gp,
*Capsella bursa-pastoris* (shephard's-purse): Cb,
*Sinapsis alba* (mustard): Sa,
*Galium aparine* (cleavers): Ga,
*Chenopodium album* (common lambsquarters): Ca, and
*Lepidium sativum* (pepperwort): Ls.

TABLE F

| | | Results of post-emergence application | | | | | | | |
|---|---|---|---|---|---|---|---|---|---|
| compound | | Act. after 7 days on | | | | Act. after 14 days on | | | |
| no | amount (g/hectare) | Gp | Cb | Sa | Ga | Gp | Cb | Sa | Ga |
| (1) | 10 | ++ | + | ++ | + | ++ | + | ++ | + |
|  | 30 | ++ | ++ | ++ | ++ | ++ | ++ | ++ | ++ |
| (2) | 10 | ++ | + | + | + | ++ | + | ± | + |
|  | 30 | ++ | + | + | ++ | ++ | + | + | ++ |
| (c) known | 10 | + | + | ± | + | + | ± | ± | + |
|  | 30 | ++ | + | + | + | ++ | + | ± | + |
| (d) known | 10 | + | ± | ± | + | + | ± | ± | + |
|  | 30 | ++ | + | ± | + | ++ | + | ± | + |

TABLE G

| | | Results of pre-emergence application | | | | | | | |
|---|---|---|---|---|---|---|---|---|---|
| compound | | Act. after 14 days on | | | | act. after 21 days on | | | |
| no. | amount (g/hectare) | Ca | Ga | Ls | Sa | Ca | Ga | Ls | Sa |
| (1) | 10 | ++ | | | | ++ | | | |
|  | 30 | ++ | ++ | | | ++ | ++ | | |
|  | 100 | | ++ | ++ | | | ++ | ++ | |
|  | 300 | | | ++ | ++ | | | ++ | ++ |
|  | 1000 | | | | ++ | | | | ++ |
| (2) | 10 | ++ | | | | ± | | | |
|  | 30 | ++ | + | | | + | + | | |
|  | 100 | | ++ | ++ | | | ++ | ++ | |
|  | 300 | | | ++ | ++ | | | ++ | + |
|  | 1000 | | | | ++ | | | | ++ |
| (c) known | 10 | ± | | | | − | | | |
|  | 30 | ++ | + | | | ± | ± | | |
|  | 100 | | ++ | ± | | | ++ | ± | |
|  | 300 | | | ++ | ± | | | ++ | − |
|  | 1000 | | | | + | | | | + |
| (d) known | 10 | + | | | | − | | | |
|  | 30 | ++ | + | | | ± | ± | | |
|  | 100 | | ++ | − | | | + | − | |
|  | 300 | | | − | − | | | + | − |
|  | 1000 | | | | ± | | | | ± |

The meanings of the above symbols are the same as in Example VII.

The above results show that the above compounds according to the invention are generally more active for controlling weeds than the known compounds.

EXAMPLE XIII

Potato and cotton desiccation

Compounds according to the invention were processed to spraying liquids according to Example VI (b).

The plants were sprayed with these liquids in the quantities tabulated below. After 2 weeks the activity with regard to leaf desiccation and, in addition for cotton, to leaf abscission was evaluated. The results are recorded in Table H. The meanings of the symbols is as follows:
- − = no or hardly any effect
- ± = obvious effect
- + = strong desiccation
- + + = complete dieing back or abscission.

TABLE H

Results of potato and cotton desiccation.

| compound | | act. on potato | | act. on cotton | | |
|---|---|---|---|---|---|---|
| no. | amount (kg/hectare) | leaves | stem | leaves | stem | leaf absc. |
| (1) | 1 | ++ | + | | | |
| (2) | 1 | ++ | + | | | |
| (3) | 1 | ± | + | + | ± | ± |
|  | 3 | + | + | + | ± | ± |
| (6) | 1 | ± | ± | ± | ± | ± |
|  | 5 | ± | ± | + | + | + |
| (7) | 1 | ± | ± | + | ± | ± |
|  | 5 | + | + | + | ± | + |

We claim:
1. An ether of the general formula

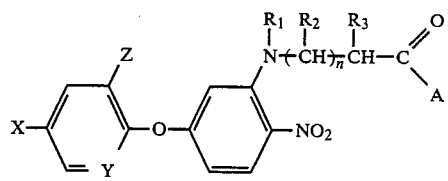

wherein
- X is a hydrogen atom, a halogen atom, a nitro group, an optionally halogenated alkyl, alkoxy or alkylthio group having 1-6 carbon atoms, or an alkanoyl group having 1-4 carbon atoms;
- Y is a nitrogen atom or a group of the formula CH or CCl;
- Z is a hydrogen atom, a halogen atom, a nitro group, an optionally halogenated alkyl group having 1-4 carbon atoms, or an alkanoyl group having 1-4 carbon atoms;
- n is 0-2;
- $R_1$ is a hydrogen atom, or an alkyl or alkanoyl group having 1-4 carbon atoms;
- $R_2$ and $R_3$ are equal or different and represent hydrogen atoms or alkyl groups having 1-4 carbon atoms; and
- A is a group of the general formula

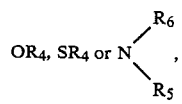

wherein
- $R_4$ is a hydrogen atom, an alkyl group having 1-6 carbon atoms, or a cation of an alkali metal, alkaline earth metal or an alkylated or non-alkylated ammonium group, and
- $R_5$ and $R_6$ are equal or different and represent hydrogen atoms, dialkylamino groups wherein the alkyl groups each have 1-4 carbon atoms, alkyl groups having 1-4 carbon atoms, or wherein
- $R_5$ and $R_6$ together with the nitrogen atom to which they are bound can form a heterocyclic ring which may comprise a second hetero atom selected from O, S or N; with the provisos, that X and Z are not both hydrogen atoms or nitro groups, and that if A is a group of the formula $OR_4$ then $R_1$ is not an alkyl group, and with the further proviso, that, if Y=CH, Z=Cl, X=$CF_3$ and n=0, then $R_1$=H and $R_3$=H or $C_1$-$C_3$ alkyl.

2. A compound as claimed in claim 1, of the general formula

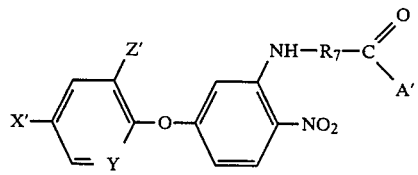

wherein
- Y has the meaning given in claim 1,
- X' is a chlorine atom, a nitro group or a trifluoromethyl group;
- Z' is a chlorine atom or a nitro group, with the proviso, that not both X' and Z' are nitro groups,
- $R_7$ is an ethylidene or ethylene group, and
- A' is a group of the general formula

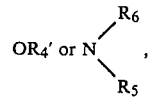

wherein
- $R_5$ and $R_6$ have the meanings given in claim 1, and
- $R_4'$ is an alkyl group having 1-4 carbon atoms.

3. A compound as claimed in claim 2, of the general formula

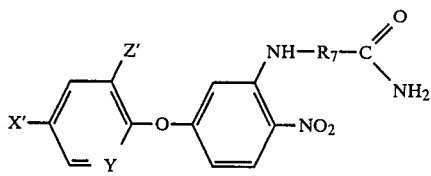

wherein
- Y has the meaning given in claim 1, and
- X', Z' and $R_7$ have the meanings given in claim 2.

4. 2-[N-{2-nitro-5-(2-chloro-4-trifluoromethylphenoxy)phenyl}-amino]propionamide.

* * * * *